(12) United States Patent
Ofer et al.

(10) Patent No.: US 11,896,317 B2
(45) Date of Patent: Feb. 13, 2024

(54) TRIANGULATION OF ITEM IN PATIENT BODY

(71) Applicant: MAZOR ROBOTICS LTD., Caesarea (IL)

(72) Inventors: Nir Ofer, Tel Aviv-Jaffa (IL); Ziv Seemann, Beit Ytzhack (IL); Dor Kopito, Kibbutz Parod (IL); Yair Schwartz, Raanana (IL); Ofir Dahan, Haifa (IL); Gal Eshed, Atlit (IL); Dvir Kadshai, Ramat Gan (IL); Amir Keret, Atlit (IL); Maor Sviri, Haifa (IL); Adi Talmor, Giva't Ada (IL); Ron Visbrot, Hadera (IL); Arie Shneiderman, Beit Rimon (IL); Aviv Ellman, Kfar Sava (IL); Gal Barazani, Haifa (IL)

(73) Assignee: MAZOR ROBOTICS LTD., Caesarea (IL)

( * ) Notice: Subject to any disclaimer, the term of this patent is extended or adjusted under 35 U.S.C. 154(b) by 830 days.

(21) Appl. No.: 16/984,514

(22) Filed: Aug. 4, 2020

(65) Prior Publication Data
US 2022/0039871 A1 Feb. 10, 2022

(51) Int. Cl.
*A61B 34/20* (2016.01)
*A61B 34/10* (2016.01)
(Continued)

(52) U.S. Cl.
CPC .............. *A61B 34/20* (2016.02); *A61B 34/10* (2016.02); *G01S 5/01* (2020.05); *G01S 5/30* (2013.01);
(Continued)

(58) Field of Classification Search
CPC ... A61B 34/20; A61B 34/10; A61B 2034/105; A61B 2034/2063; A61B 34/25;
(Continued)

(56) References Cited

U.S. PATENT DOCUMENTS 4,870,623 A * 9/1989 Buckley .............. G01S 15/8913
367/103
6,695,785 B2 2/2004 Brisken et al.
(Continued)

FOREIGN PATENT DOCUMENTS

EP 3632333 4/2020
KR 10-2008-0043921 5/2008
(Continued)

OTHER PUBLICATIONS

Bianchi et al. "Localization strategies for robotic endoscopic capsules: a review," Expert Review of Medical Devices, 2019, vol. 16, No. 5, pp. 381-403.
(Continued)

*Primary Examiner* — Daniel Pihulic
(74) *Attorney, Agent, or Firm* — Sheridan Ross P.C.

(57) ABSTRACT

A surgical positioning system includes an emitter secured to a medical implant; at least three microphones; at least one processor; and a memory. The emitter has a speaker and a power source. The memory stores instructions for execution by the processor that, when executed, cause the processor to receive, from each of the at least three microphones, information about a detected sound; and calculate, based on position information corresponding to each of the at least three microphones and the received information, a position of the implant.

20 Claims, 4 Drawing Sheets

(51) Int. Cl.
*G01S 5/00* (2006.01)
*G01S 5/30* (2006.01)

(52) U.S. Cl.
CPC . *A61B 2034/105* (2016.02); *A61B 2034/2063* (2016.02)

(58) Field of Classification Search
CPC ............ A61B 2034/2048; A61B 34/30; A61B 2034/102; A61B 2034/2055; A61B 2034/2059; G01S 5/01; G01S 5/30
See application file for complete search history.

(56) References Cited

U.S. PATENT DOCUMENTS

| | | | |
|---|---|---|---|
| 6,716,166 | B2 | 4/2004 | Govari |
| 6,826,421 | B1 | 11/2004 | Beatty et al. |
| 7,314,446 | B2 | 1/2008 | Byrd et al. |
| 7,549,960 | B2 | 6/2009 | Govari |
| 7,796,789 | B2 | 9/2010 | Salgo et al. |
| 8,010,181 | B2 | 8/2011 | Smith et al. |
| 8,175,680 | B2 | 5/2012 | Panescu |
| 8,685,093 | B2 | 4/2014 | Anderson et al. |
| 9,220,488 | B2 | 12/2015 | Emery et al. |
| 10,507,006 | B2 | 12/2019 | Samset et al. |
| 10,639,004 | B2 | 5/2020 | Byrd et al. |
| 2003/0093067 | A1 | 5/2003 | Panescu |
| 2005/0203375 | A1 | 9/2005 | Willis et al. |
| 2005/0261571 | A1 | 11/2005 | Willis et al. |
| 2006/0098534 | A1* | 5/2006 | Hickling ............... G01S 3/8006 73/594 |
| 2006/0116576 | A1 | 6/2006 | McGee et al. |
| 2013/0172907 | A1 | 7/2013 | Harris |
| 2013/0225983 | A1 | 8/2013 | Willis et al. |
| 2017/0007199 | A1 | 1/2017 | Bourlion et al. |
| 2017/0043128 | A1 | 2/2017 | Hu |
| 2017/0367579 | A1 | 12/2017 | Reiner |
| 2018/0036513 | A1 | 2/2018 | Cruz, Jr. et al. |
| 2019/0015070 | A1 | 1/2019 | Memon et al. |
| 2019/0261944 | A1 | 8/2019 | Stapert et al. |
| 2019/0307419 | A1 | 10/2019 | Durfee |
| 2022/0039871 | A1* | 2/2022 | Ofer ....................... A61B 34/30 |

FOREIGN PATENT DOCUMENTS

| | | | |
|---|---|---|---|
| WO | WO 2009/042644 | 4/2009 | |
| WO | WO-2010048205 A1 * | 4/2010 | ............... G01S 5/22 |
| WO | WO 2014/164363 | 10/2014 | |
| WO | WO 2019/147857 | 8/2019 | |
| WO | WO-2022029758 A1 * | 2/2022 | ............. A61B 34/10 |

OTHER PUBLICATIONS

Umay et al. "Localization and Tracking of Implantable Biomedical Sensors," Sensors, 2017, vol. 17, No. 3, Article 583, 20 pages.
International Search Report and Written Opinion for International (PCT) Patent Application No. PCT/IL2021/050899, dated Nov. 24, 2021, 17 pages.

\* cited by examiner

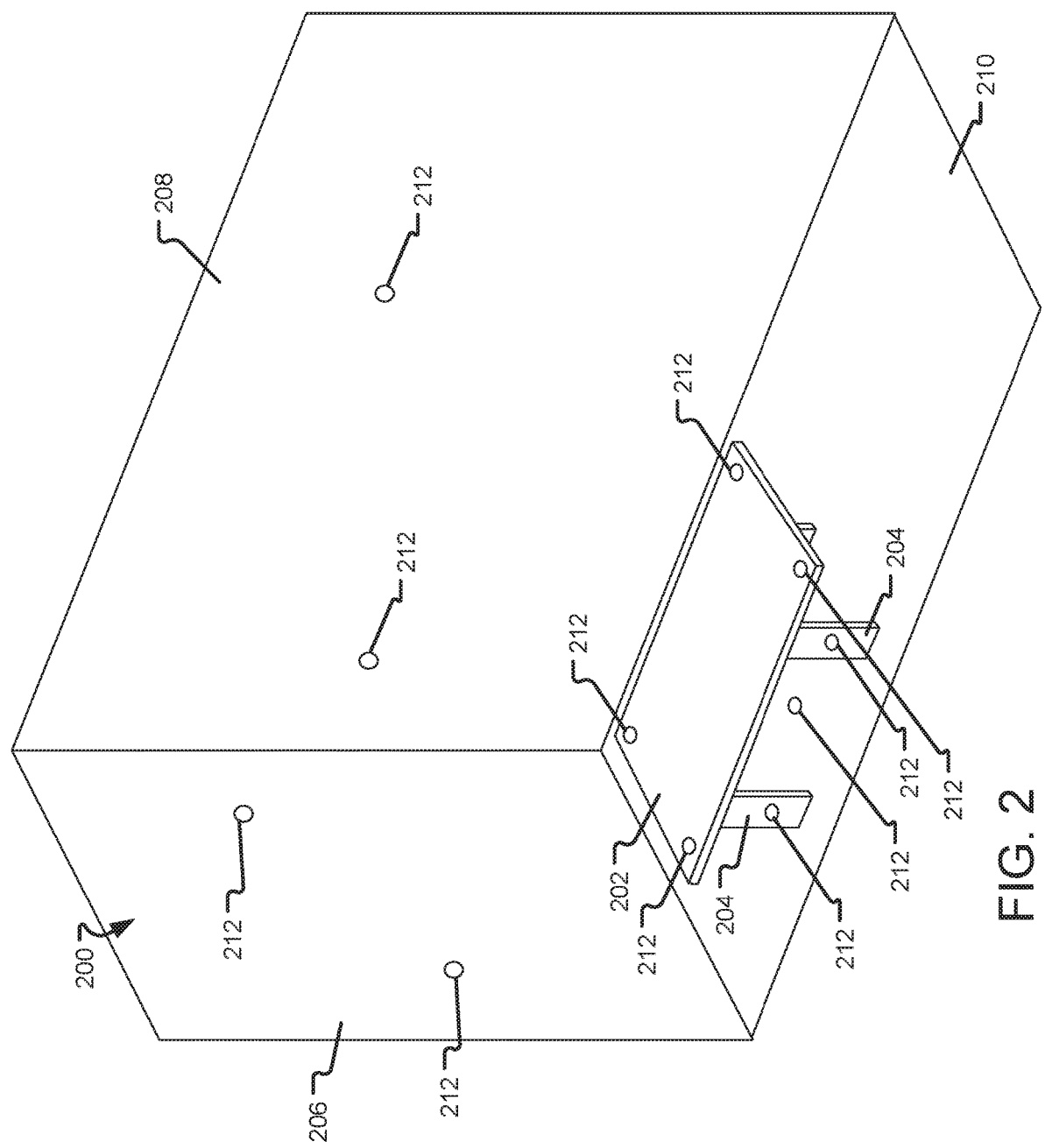
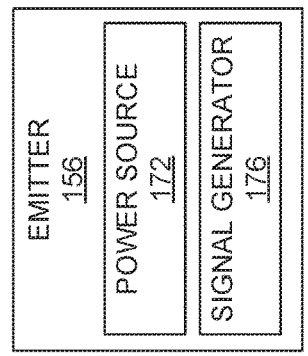

TRIANGULATION OF ITEM IN PATIENT BODY

FIELD

The present technology generally relates to surgery, and relates more particularly to object location and tracking during surgery.

BACKGROUND

X-ray imaging is used determine the position of an object that is within a patient's body and therefore not optically visible, including both anatomical features of the patient (e.g., bones or features thereof) and medical devices (e.g., implants, tools). Navigation systems may be used to determine the position of such objects if a reference marker is secured to the object and extends out of the body, so as to be visible to a navigation camera.

SUMMARY

Aspects of the present disclosure include:

A surgical positioning system, comprising: an emitter secured to a medical implant; at least three microphones; at least one processor; and a memory. The emitter comprises a speaker and a power source. The memory stores instructions for execution by the processor that, when executed, cause the processor to: receive, from each of the at least three microphones, information about a detected sound; and calculate, based on position information corresponding to each of the at least three microphones and the received information, a position of the implant.

Any of the aspects herein, wherein the memory stores additional instructions for execution by the at least one processor that, when executed, further cause the at least one processor to: receive a model of a portion of a patient's anatomy; and calculate, based on the model, a predicted speed of sound through at least a segment of the portion of the patient's anatomy.

Any of the aspects herein, wherein the memory stores additional instructions for execution by the at least one processor that, when executed, further cause the at least one processor to update the predicted speed of sound based on calibration data corresponding to a calibration sound generated by the emitter and detected by each of the at least three microphones.

Any of the aspects herein, wherein the calculating the position of the implant is further based on the updated predicted speed of sound.

Any of the aspects herein, wherein each of the at least three microphones is mounted in a fixed position relative to any others of the at least three microphones.

Any of the aspects herein, wherein the detected sound has a frequency less than 20 kHz.

Any of the aspects herein, wherein the detected sound has a frequency less than 20 Hz.

Any of the aspects herein, wherein at least one of the at least three microphones is mounted to a movable arm, and the memory stores additional instructions for execution by the at least one processor that, when executed, further cause the at least one processor to: receive arm position data corresponding to a position of the movable arm; and calculate, based at least in part on the arm position data, a location of each of the at least three microphones.

Any of the aspects herein, wherein the position information for each of the at least three microphones comprises data about a position of each of the at least three microphones relative to the others of the at least three microphones, and the calculated emitter position is relative to the positions of the at least three microphones.

Any of the aspects herein, wherein the position information for each of the at least three microphones is relative to a common coordinate system.

Any of the aspects herein, wherein the emitter comprises a plurality of speakers, each speaker is configured to emit sound at a different frequency than the other speakers in the plurality of speakers, the received information comprises information about a detected sound generated by each of the plurality of speakers, respectively, and the memory stores additional instructions for execution by the at least one processor that, when executed, further cause the at least one processor to determine an orientation of the implant based at least in part on the received information.

A method of locating an object during a surgery, comprising: receiving a model of a portion of a patient's anatomy; receiving a surgical plan comprising information about a planned position of an implant within the portion of the patient's anatomy; calculating, based on the planned position of the implant and the model, a predicted speed of sound along at least one path that extends at least partially through the portion of the patient's anatomy; receiving, from at least three microphones, detection information about a detected sound generated by a speaker secured to the implant; and determining, based on the predicted speed of sound and the detection information, a position of the implant.

Any of the aspects herein, wherein the detection information comprises first detection information about a first detected sound generated by the speaker at a first time, and further comprising: receiving, from the at least three microphones, second detection information about a second detected sound generated by the speaker, the second detected sound generated at a second time after the first time; and determining, based on first detection information and the second detection information, a movement of the implant.

Any of the aspects herein, wherein the detection information corresponds to detected sounds generated by a plurality of speakers secured to the implant, and further comprising: determining, based on the predicted speed of sound and the detection information, an orientation of the implant.

Any of the aspects herein, wherein each of the detected sounds has a unique frequency relative to any others of the detected sounds.

Any of the aspects herein, wherein the determining is further based on location information corresponding to a location of each of the at least three microphones.

Any of the aspects herein, wherein the detection information comprises first detection information about a first detected sound generated by the speaker at a first time, the method further comprising: receiving, from the at least three microphones, second detection information about a second detected sound generated by a second speaker affixed to an anatomical element of the patient; and determining, based on first detection information and the second detection information, a position of the implant relative to the anatomical element.

A surgical triangulation system comprising: a plurality of microphones configured to be installed in fixed locations about an operating room; an emitter configured to be secured to an internal anatomical feature of a patient or an implant; at least one processor; and a memory. The emitter comprises a speaker and a power source. The memory stores instructions for execution by the at least one processor that, when executed, cause the at least one processor to: receive a surgical plan comprising information about a portion of the patient's anatomy; receive, from the plurality of microphones, sound information about a sound detected by the plurality of microphones and generated by the speaker; and calculate, based on the surgical plan, the sound information, and information about the fixed locations of the plurality of microphones, a position of the emitter.

Any of the aspects herein, wherein the emitter is biocompatible.

Any of the aspects herein, wherein the emitter comprises a second speaker, and the memory stores additional instructions for execution by the at least one processor that, when executed, further cause the at least one processor to: receive, from the plurality of microphones, second sound information about a second sound detected by the plurality of microphones and generated by the second speaker; and calculate, based on the surgical plan, the second sound information, and the information about the fixed locations of the plurality of microphones, an orientation of the emitter.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 1B is a block diagram of an emitter according to at least one embodiment of the present disclosure;

FIG. 2 is an illustration of an operating room;

DETAILED DESCRIPTION

Figure 1A:
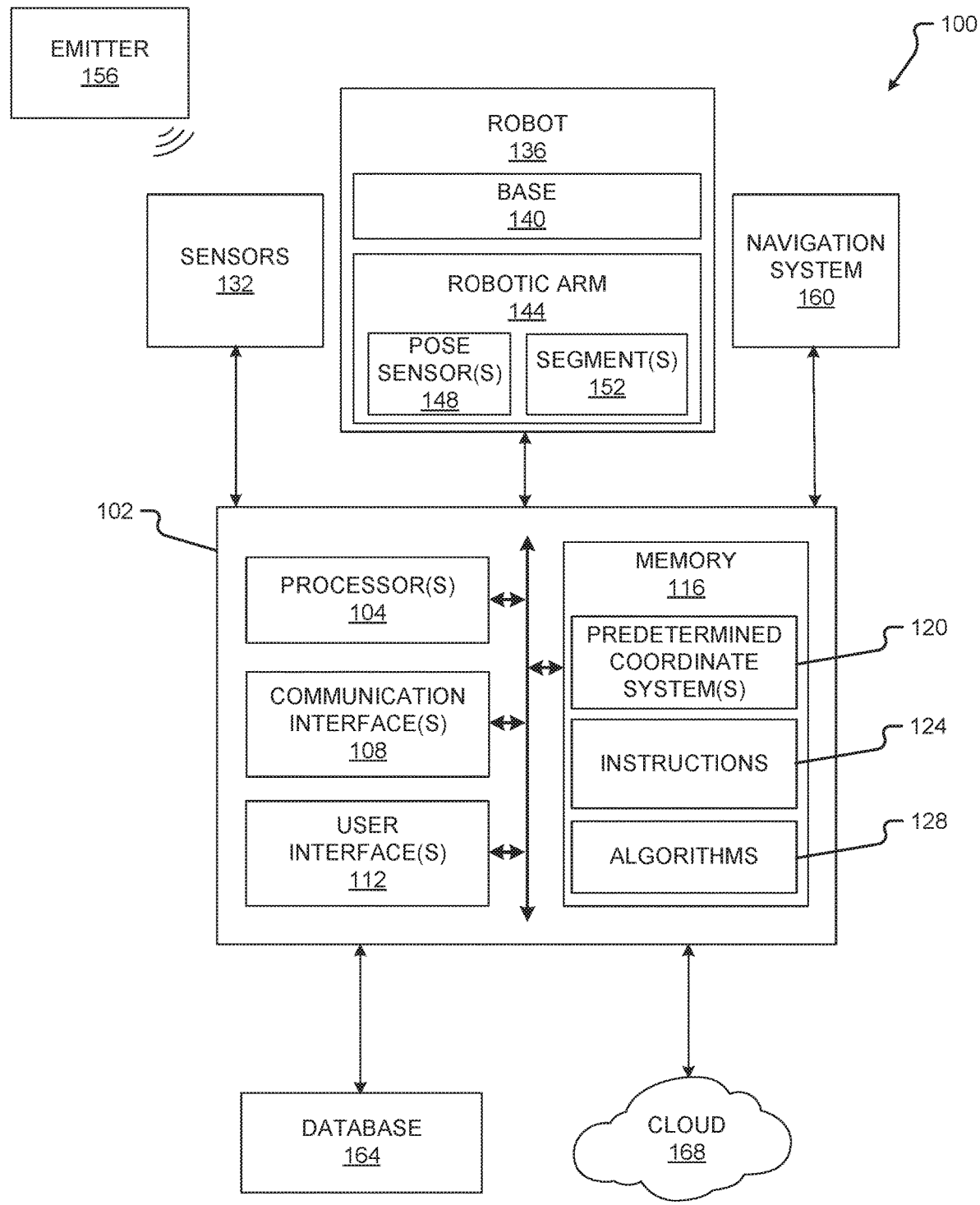
FIG. 1A is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Existing methods of locating an object within a patient's body—whether the object is a foreign object, such as a medical device or tool (including, for example, a medical implant), or a native object, such as an anatomical feature of the patient (including, for example, a bone or organ within the patient)—include x-ray imaging, which exposes the patient and the operating room staff to harmful radiation, and ultrasound imaging, which requires an ultrasound probe to be positioned adjacent the patient's skin and aimed at the object in question. There remains a need, for example, to locate an object within a patient's body without the use of a system or device that emits harmful radiation, and more conveniently than may be accomplished using ultrasound.

According to some embodiments of the present disclosure, a small chip or resonance item (which may be, for example, a speaker) may be attached, affixed, or otherwise secured to an object to be traced or tracked, such as a medical implant, a medical tool, a bone, or any other object within (or to be placed within) the patient's body. In some embodiments, the small chip may be removably secured to the object, while in other embodiments, the small chip may be permanently secured to the object, contained within the object, or otherwise configured to remain on or within the object. Also according to some embodiments of the present disclosure, a plurality of devices may be positioned outside of the patient's body, and configured to send and/or receive one or more signals from the small chip or resonance item. For example, in embodiments where the small chip or resonance item is or comprises a speaker, each of the plurality of devices may be a microphone. The plurality of devices may be positioned at known locations relative to each other, and/or at known locations within a common coordinate system. Each of the plurality of devices may comprise one or more sensors for accurately measuring a distance to any others of the plurality of devices or for determining a position thereof within a coordinate system. Each of the plurality of devices may be secured in a fixed location, or one or more of the plurality of devices may be movable. In the latter instance, a position of each of the plurality of devices (or at least of any movable device) may be determined after the device is moved, whether using one or more sensors on the device itself, one or more sensors on an arm or other object that is holding the device, or otherwise.

The plurality of devices may transmit a signal to the small chip or resonance item, which may return the signal (or transmit another signal in response to the first signal). Upon receipt of the return or other signal from the small chip or resonance item by the plurality of devices, a processor may be used to triangulate the position of the small chip or resonance item (e.g., based on the time of flight of the signals, or otherwise). Error in the system may be reduced by increasing the number of the plurality of devices, and/or by adding more small chips or resonance items to the object.

According to at least one embodiment of the present disclosure, ultrasound may be used for triangulation. Ultrasound has good angular accuracy. In embodiments that use ultrasound, a truss with a flexible joint and one or more encoders may be used to achieve accuracy.

According to at least another embodiment of the present disclosure, wireless signals may be used for triangulation, including radio frequency signals, WiFi signals, ZigBee signals, Bluetooth signals, Bluetooth low energy signals, Bluetooth beacon signals, GSM signals, LTE signals, and signals using any other wireless communication protocol. In some embodiments, no wireless communication protocol is needed. A plurality of transceivers may be located outside of the patient's body, and configured to ping the small chip or resonance item inside of the patient's body, then receive a return signal from the small chip or resonance item. Error can be reduced by changing which one of the plurality of transceivers transmits the signal and by using all of the transceivers in the array to receive the return signal. High-speed processing may be utilized to facilitate triangulation using wireless signals (or any other method of triangulation described herein).

According to at least another embodiment of the present disclosure, triangulation may be accomplished using sound. For example, a small ceramic 'speaker' may be placed on an implant or medical tool or other element to be tracked. An array of microphones may be positioned outside of the patient's body, each microphone configured to detect sound waves at the frequency or frequencies at which the speaker is configured to generate such sound waves. One or more frequencies may be chosen, for example, based on which frequencies move best through anatomical tissue. Multiple frequencies may be used to achieve better accuracy.

According to still other embodiments of the present disclosure, a plurality of triangulation methods may be used simultaneously or together to improve accuracy. Additionally, in some embodiments the small chip or resonance item may be passive (e.g., configured only to reflect signals generated outside the patient's body) or active (e.g., configured to generate signals that may be detected outside the patient's body). Accuracy may be increased by increasing the number of devices positioned outside of the patient's body, and/or by utilizing a plurality of small chips or resonance items on the implant, tool, or other item inside the patient's body.

Embodiments of the present disclosure beneficially enable more accurate placement of implants and tools in a patient's body. Embodiments of the present disclosure also beneficially enable position determination and tracking without exposing the patient or any attending physicians or other operating room staff to harmful radiation. Embodiments of the present disclosure further beneficially enable position determination and tracking without requiring a line of sign to the tracked object or to a reference marker attached to the tracked object.

Turning first to FIG. 1A, a block diagram of a system 100 according to at least one embodiment of the present disclosure is shown. The system 100 may be used, for example: to locate an object within a patient's body, whether that object is a foreign object (e.g., a medical tool, implant, or other device) or an anatomical feature of the patient (e.g., a bone or organ); to determine an orientation of an object within a patient's body; to detect movement or relative movement of an object within a patient's body; for autonomous surgery; for robot-assisted surgery; to calibrate a triangulation system; to verify the operational integrity of a navigation system using an independent triangulation system and/or vice versa; to carry out one or more aspects of one or more of the methods disclosed herein; or for any other useful purpose. The system 100 comprises a computing device 102, a plurality of sensors 132, a robot 136, an emitter 156, a navigation system 160, a database 164, and a cloud 168. Notwithstanding the foregoing, systems according to other embodiments of the present disclosure may omit any one or more of the computing device 102, the plurality of sensors 132, the robot 136, the emitter 156, the navigation system 160, the database 164, and/or the cloud 168. Additionally, systems according to other embodiments of the present disclosure may arrange one or more components of the system 100 differently (e.g., one or more of the plurality of sensors 132, the robot 136, and the navigation system 160 may comprise the components shown in FIG. 1A as being part of the computing device 102).

The computing device 102 comprises at least one processor 104, at least one communication interface 108, at least one user interface 112, and at least one memory 116. A computing device according to other embodiments of the present disclosure may omit one or both of the communication interface(s) 108 and the user interface(s) 112.

The at least one processor 104 of the computing device 102 may be any processor identified or described herein or any similar processor. The at least one processor 104 may be configured to execute instructions stored in the at least one memory 116, which instructions may cause the at least one processor 104 to carry out one or more computing steps utilizing or based on data received, for example, from the plurality of sensors 132, the robot 136, the emitter 156, the navigation system 160, the database 164, and/or the cloud 168.

The computing device 102 may also comprise at least one communication interface 108. The at least one communication interface 108 may be used for receiving image data or other information from an external source (such as the plurality of sensors 132, the robot 136, the navigation system 160, the database 164, the cloud 168, and/or a portable storage medium (e.g., a USB drive, a DVD, a CD)), and/or for transmitting instructions, images, or other information from the at least one processor 104 and/or the computing device 102 more generally to an external system or device (e.g., another computing device 102, the robot 136, the navigation system 160, the database 164, the cloud 168, and/or a portable storage medium (e.g., a USB drive, a DVD, a CD)). The at least one communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, Bluetooth low energy, NFC, ZigBee, and so forth). In some embodiments, the at least one communication interface 108 may be useful for enabling the device 102 to communicate with one or more other processors 104 or computing devices 102, whether to reduce the time needed to accomplish a computing-intensive task or for any other reason.

The at least one user interface 112 may be or comprise a keyboard, mouse, trackball, monitor, television, touchscreen, button, joystick, switch, lever, and/or any other device for receiving information from a user and/or for providing information to a user of the computing device 102. The at least one user interface 112 may be used, for example, to receive a user selection or other user input in connection with any step of any method described herein; to receive a user selection or other user input regarding one or more configurable settings of the computing device 102 and/or of another component of the system 100; to receive a user selection or other user input regarding how and/or where to store and/or transfer data received, modified, and/or generated by the computing device 102; and/or to display information (e.g., text, images) and/or play a sound to a user based on data received, modified, and/or generated by the computing device 102. Notwithstanding the inclusion of the at least one user interface 112 in the system 100, the system 100 may automatically (e.g., without any input via the at least one user interface 112 or otherwise) carry out one or more, or all, of the steps of any method described herein.

Although the at least one user interface 112 is shown as part of the computing device 102, in some embodiments, the computing device 102 may utilize a user interface 112 that is housed separately from one or more remaining components of the computing device 102. In some embodiments, the user interface 112 may be located proximate one or more other components of the computing device 102, while in other embodiments, the user interface 112 may be located remotely from one or more other components of the computer device 102.

The at least one memory 116 may be or comprise RAM, DRAM, SDRAM, other solid-state memory, any memory described herein, or any other tangible non-transitory memory for storing computer-readable data and/or instructions. The at least one memory 116 may store information or data useful for completing, for example, any step of the methods 300 and/or 400 described herein. The at least one memory 116 may store, for example, information about one or more predetermined coordinate systems 120 (e.g., information about a robotic coordinate system or space, information about a navigation coordinate system or space, information about a patient coordinate system or space); instructions 124 for execution by the at least one processor 104, for example to cause the at least one processor 104 to carry out one or more of the steps of the method 300 and/or of the method 400; and/or one or more algorithms 128 for use by the processor in carrying out any calculations necessary to complete one or more of the steps of the method 300 and/or of the method 400, or for any other calculations. Such predetermined coordinate system(s) 120, instructions 124, and/or algorithms 128 may, in some embodiments, be organized into one or more applications, modules, packages, layers, or engines, and may cause the at least one processor 104 to manipulate data stored in the at least one memory 116 and/or received from or via another component of the system 100.

The plurality of sensors 132 are configured to detect one or more signals generated or reflected by the emitter 156. The plurality of sensors may be positioned at fixed and known locations on or around an operating table, within an operating room, on one or more stands or other objects within an operating room, and/or in any other location suitable for receiving and/or detecting one or more signals generated or reflected by the emitter 156. In some embodiments, the plurality of sensors 132 comprises at least one sensor 132 configured to generate a signal, which may then be reflected by the emitter 156 and detected or otherwise received by the plurality of sensors 132. In some embodiments, the plurality of sensors may comprise three sensors. In other embodiments, the plurality of sensors may comprise more than three sensors. The sensors may be spread around an operating room or other surgical environment to increase a likelihood that at least three sensors of the plurality of sensors 132 will detect or receive a signal from the emitter 156. In some embodiments, one or more of the plurality of sensors 132 may be positioned on or adjacent a patient's skin, while in other embodiments, none of the plurality of sensors 132 may be positioned on or adjacent to the patient's skin. The plurality of sensors 132 may be or comprise microphones, wireless receivers or transceivers (configured, for example, to receive radio frequency signals of any variety or generated using any protocol or no protocol), ultrasound probes, RADAR probes, SONAR probes, any other device capable of receiving a signal, and/or any combination of two or more of the foregoing.

The plurality of sensors 132 may be or comprise directional sensors configured to determine a direction from which a signal is detected.

Although not shown in the figures, in some embodiments, the system 100 may comprise a plurality of emitters 156 and a single sensor 132, and the single sensor 132 may be configured to be placed within a patient's body to detect a signal generated or reflected by the plurality of emitters 156 and to communicate, whether via the sensors 132, the communication interface(s) 108, or otherwise, with the computing device 102.

In embodiments where the plurality of sensors 132 are located in fixed positions (e.g., mounted to a wall, ceiling, and/or floor of an operating room, and/or to a fixed operating table, or to one or more non-moveable stands or structures), information about the fixed positions in which the plurality of sensors 132 are located may be stored, for example, in the memory 116. Such information may be relative to one or more predetermined coordinate system(s) 120 stored in the memory 116.

In some embodiments, one or more of the plurality of sensors 132 may be moveable, whether by virtue of being secured to or held by a moveable stand, secured to or held by a robotic arm or an articulated arm, or otherwise. In embodiments where one or more of the plurality of sensors 132 are secured to or held by a robotic arm, the robotic arm may be precisely moveable (e.g., such that the precise position of a given point on the robotic arm is known at any given time during operation thereof), so that a position of the one or more sensors 132 is known regardless of the pose of the robotic arm. In embodiments of the present disclosure comprising one or more moveable sensors 132, the location of any such moveable sensors 132 may be determined once the sensor 132 is positioned (and, thereafter, any time the moveable sensor 132 is repositioned), whether using one more sensors on the moveable stand, the robotic arm or articulated arm, or otherwise; using manual measuring techniques; using a calibration process (which may or may not utilize triangulation methods); or otherwise.

The greater the number of sensors included in the plurality of sensors 132, the greater the accuracy of any triangulation calculations may be. Additionally, the more spread out the sensors included in the plurality of sensors 132, the greater the accuracy of any triangulation calculations may be. The plurality of sensors 132 may comprise at least three sensors, or at least four sensors, or at least five sensors, or at least ten sensors.

Although shown in FIG. 1A as being in communication only with the computing device 102, in some embodiments, the plurality of sensors 132 may be in communication with any one or more of the computing device 102, the robot 136, the navigation system 160, the database 164, and/or the cloud 168.

The plurality of sensors 132 may be configured to receive and/or detect only signals generated or reflected by the emitter 156. For example, where the plurality of sensors 132 comprises one or more microphones and the emitter 156 comprises one or more speakers, the one or more microphones may be configured to receive or detect only sounds at one or more specific frequencies. Such a configuration of the plurality of sensors 132 may beneficially reduce the amount of noise detected by the plurality of sensors 132, reduce the amount of processing power needed to interpret any received or detected signals, and/or improve the accuracy of the results of any triangulation process. The plurality of sensors 132 may be configured to continuously receive and/or detect signals from the emitter 156, or may be configured to receive and/or detect such signals only when activated (whether manually or autonomously, or according to a predetermined schedule), or otherwise.

The robot 136 may be any surgical robot or surgical robotic system. The robot 136 may be or comprise, for example, the Mazor X™ Stealth Edition robotic guidance system. The robot 136 may comprise a base 140 that supports a single robotic arm 144. The robot 136 may comprise one or more robotic arms 144. In some embodiments, the robotic arm 144 may comprise a first robotic arm and a second robotic arm. In other embodiments, the robot 136 may comprise more than two robotic arms 144. The robotic arm 144 may, in some embodiments, assist with a surgical procedure (e.g., by holding a tool in a desired trajectory or pose and/or supporting the weight of a tool while a surgeon or other user operates the tool, or otherwise) and/or automatically carry out a surgical procedure.

The robotic arm 144 may have three, four, five, six, seven, or more degrees of freedom. The robotic arm 144 may comprise one or more segments 152. Each segment 152 may be secured to at least one adjacent member by a joint, such that the robotic arm is articulated. The joint(s) may be any type of joint that enables selective movement of the member relative to the structure to which the joint is attached (e.g., another segment of the robotic arm, or the base 140). For example, the joint may be a pivot joint, a hinge joint, a saddle joint, or a ball-and-socket joint. The joint may allow movement of the member in one dimension or in multiple dimensions, and/or along one axis or along multiple axes.

While a proximal end of the robotic arm 144 may be secured to the base 140 (whether via a joint or otherwise), a distal end of the robotic arm 144 may support an end effector. The end effector may be, for example, a tool (e.g., a drill, saw, imaging device) or a tool guide (e.g., for guiding a biopsy needle, ablation probe, or other tool along a desired trajectory).

The robotic arm 144 may comprise one or more pose sensors 148. The pose sensors 148 may be configured to detect a pose of the robotic arm, and may be or comprise one or more rotary encoders, linear encoders, incremental encoders, or other sensors. Data from the pose sensors 148 may be provided to a processor of the robot 136, to the processor 104 of the computing device 102, and/or to the navigation system 160. The data may be used to calculate a position in space of the robotic arm 144 relative to a predetermined coordinate system. Such a calculated position may be used, for example, to determine a position in space of one or more of the plurality of sensors 132 that are attached to the robotic arm 144.

With reference still to FIG. 1A, and also to FIG. 1B, the emitter 156 is configured to be attached to a medical implant, a surgical tool, an anatomical feature of a patient, or any other object inside or to be placed inside of a patient. The emitter 156 may be configured to generate or reflect one or more signals receivable and/or detectable by the plurality of sensors 132. In embodiments where the emitter 156 is configured only to reflect signals generated by a device other than the emitter 156, the emitter 156 may be passive and/or unpowered, and may be made of a material and/or fashioned with a shape that will enhance reflectivity thereof. For example, the emitter 156 may be configured to reflect ultrasound waves, or to reflect radio frequency waves, or as a RADAR target or a SONAR target. In such embodiments, the emitter 156 may be unpowered.

In embodiments where the emitter 156 is configured to generate one or more waves or other signals, the emitter 156 may be powered. In such embodiments, the emitter 156 may comprise a power source 172. The power source 172 may be, for example, a lithium iodide battery or any other battery or fuel cell suitable for use and/or implantation in a patient (whether within a protective housing or otherwise).

The emitter 156 may also comprise a signal or wave generator 176, which may be a speaker (where sound waves will be used for triangulation), a radio transmitter (where RF signals will be used for triangulation), or any other transmitter or generator. Where the signal generator 176 is a speaker, the speaker may be configured to generate sound waves at a single frequency, or to selectively generate sound waves at one of a plurality of predetermined frequencies. The speaker may be configured to generate sound waves at any frequency within the sonic spectrum. In some embodiments, the speaker may be configured to generate sound waves only at or below the acoustic spectrum (e.g., at frequencies less than 20 kHz). In other embodiments, the speaker may be configured to generate sound waves only within the infrasound spectrum (e.g., lower than 20 Hz). In still other embodiments, the speaker may be configured to generate sound waves in the ultrasound spectrum (e.g., higher than 20 kHz). In still other embodiments, the speaker may be configured to generate sound waves only outside of the acoustic spectrum (e.g., below 20 Hz and above 20 kHz). Use of sound waves outside of the acoustic spectrum may beneficially enable the system 100 to avoid generating sounds that are audible to operating room staff and/or to avoid sounds generated by operating room staff from being picked up by the plurality of sensors 132 and confused (e.g., by the processor 102) for sounds generated by the emitter 156.

Where the signal generator 176 is a speaker, the speaker may be a ceramic speaker. The speaker may be a piezoelectric speaker. The speaker may have a maximum dimension (e.g., length or width or height) of less than one quarter of one inch, or of less than half of one inch, or of less than one inch, or less than one and one half inches.

The signal generator 176 may be configured to generate a signal at a periodic interval (e.g., every second, every five seconds, every ten seconds, every twenty seconds, every thirty seconds, every minute, every five minutes, every thirty minutes, or on any other interval). The signal generator 176 may also be configured to generate a signal only in response to an external stimulus (which may be, for example, a signal received from an external source by the emitter 156). In such embodiments, the emitter 156 may comprise a receiver configured to receive and/or detect such signals, and/or a processor or other logic (implemented in software and/or in hardware) configured to cause the signal generator 176 to generate a signal in response to receipt of the a signal. The emitter 156 may also comprise one or more sensors (e.g., an accelerometer or other sensor) configured to detect a movement of the emitter 156 and/or any other one or more environmental characteristics relevant to the emitter 156, and may comprise a processor or other logic (implemented in software and/or in hardware) configured to cause the signal generator to generate a signal in response to one or more predetermined environmental conditions.

In some embodiments, the emitter 156 may comprise a plurality of signal generators 176. In such embodiments, the signal generators 176 may be positioned as far from each other on or within the emitter 156 as possible, and may be configured to generate signals having slightly different characteristics. For example, where the signal generators 176 are speakers, each speaker may be configured to generate sound waves having a slightly different frequency (e.g., one speaker may be configured to generate a sound wave at 100 Hz, while another may be configured to generate a sound wave at 102 Hz). Of course, larger variations are possible as well; one speaker may be configured to generate a sound wave at 20 Hz, and another may be configured to generate a sound wave at 20 kHz. In such embodiments, triangulation may be used to calculate a position of each of the plurality of signal generators 176, and the calculated positions may then be used to determine an orientation of the emitter 156. As may be appreciated, an orientation of the emitter 156 determined based on the calculated positions of two separate signal generators 176 will be less precise than an orientation of the emitter 156 determined based on the calculated positions of three or more separate signal generators 176.

The emitter 156 may comprise a housing in which the power source 172 and signal generator 176 are stored. The housing may protect the power source 172 and the signal generator 176 from bodily fluids and other environmental conditions internal to the body of a patient in which the emitter 156 is placed (whether temporarily or permanently). The housing may also protect the patient from the power source 172 and/or the signal generator 176. In some embodiments, the emitter 156 may be biocompatible by virtue of such a housing, while in other embodiments the components of the emitter 156 may themselves be biocompatible, and no housing may be needed.

The emitter 156 may be or comprise a device or mechanism for securing the emitter 156 to a medical implant, surgical tool, anatomical feature, or other object within or to be inserted within a patient's body. The emitter 156 may be configured to be attached to such an object using one or more screws or other mechanical fasteners, or using an adhesive, or using stiches, or using staples, or using any other fastening or securing mechanism. In some embodiments, an implant or surgical tool may be manufacturing with an emitter 156 (or with one or components of an emitter 156) contained within the implant, such that the implant acts as a housing for the emitter 156 or for the one or more components thereof. In some embodiments, the emitter 156 may be configured to be secured within a hole drilled into or otherwise fashioned in an implant, tool, anatomical feature, or other object, whether by way of a friction fit or otherwise. The emitter 156 is configured to be fixedly secured to an object, so that determination of a position of the emitter enables determination of a position of the object. The emitter 156 may be permanently secured to the object, or removably secured to the object. In some embodiments, the emitter 156 may be safely left within the body of the patient.

Some embodiments of the system 100 may comprise more than one emitter 156. In such embodiments, multiple emitters 156 may be secured to a single object (e.g., to better determine an orientation of the object), and/or one or more emitters 156 may be secured to more than one object (e.g., in order to determine a position of more than one object within the patient's body, and/or to determine relative movement between or among the more than one object).

Referring again to FIG. 1A, the navigation system 160 may provide navigation for a surgeon and/or for the robot 136 during an operation or surgical procedure. The navigation system 160 may be any now-known or future-developed navigation system, including, for example, the Medtronic StealthStation™ S8 surgical navigation system. The navigation system 160 may include a camera or other sensor(s) for detecting and/or tracking one or more reference markers, navigated trackers, or other objects within an operating room or other room where a surgical procedure takes place. In some embodiments, the navigation system 160 may comprise the plurality of sensors 132. In various embodiments, the navigation system 160 may be used to track a position of the robotic arm 144 and/or one or more other objects to which the navigation system 160 has a line of sight (where the navigation system is an optical system) or that are otherwise detectable by the navigation system 160. The navigation system 160 may be used to track a position of one or more reference markers or arrays or other structures useful for detection by a camera or other sensor of the navigation system 160. The navigation system 160 may include a display for displaying one or more images from an external source (e.g., the computing device 102, plurality of sensors 132, or other source) or a video stream from the camera or other sensor of the navigation system 160. In some embodiments, the system 100 may operate without the use of the navigation system 160.

The database 164 may store information about a given operation or surgical procedure, such as one or more surgical plans, one or more digital models of a portion of a patient's anatomy, one or more digital models of implants, tools, or other objects (anatomical features or foreign objects) that may be located or positioned within a patient's body, one or more images of a patient's anatomy, and/or any other useful information. Any data described above as being stored within the memory 116 may also or alternatively be stored within the database 164, and vice versa. The database 164 may be configured to provide any information stored therein to the computing device 102 or to any other device of the system 100 or external to the system 100, whether directly or via the cloud 168. In some embodiments, the database 164 may be or comprise part of a hospital image storage system and/or electronic health records system, such as a picture archiving and communication system (PACS), a health information system (HIS), and/or another system for collecting, storing, managing, and/or transmitting electronic medical records including image data.

The cloud 168 may be or represent the Internet or any other wide area network. The computing device 102 may be connected to the cloud 168 via the communication interface 108, using a wired connection, a wireless connection, or both. In some embodiments, the computing device 102 may communicate with the database 164 and/or an external device (e.g., a computing device) via the cloud 168.

Turning now to FIG. 2, a plurality of sensors 212 (which may be the same as or similar to the plurality of sensors 132) may be installed in any number of fixed locations around an operating room 200, including for example on an operating table 202 (on which a patient may lay during a surgical procedure), one or more legs 204 of the operating table 202, a wall 206 or 208 of the operating room, a floor 210 of the operating room, and/or a ceiling of the operating room (not shown). The plurality of sensors 212 may be spread around the operating room to increase an accuracy of any triangulation calculations. The plurality of sensors 212 may be positioned to increase a likelihood that at least a minimum number of sensors 212 (e.g., three sensors 212) will receive and/or detect a signal generated or reflected by an emitter 156.

In some embodiments, an array of sensors 212 may be mounted to a fixed frame that is configured to be mounted to a wall 206 or 208, mounted to or hung from a ceiling of an operating room, or otherwise positioned within an operating room. The array of sensors 212 may beneficially comprise at least three sensors having known positions relative to each other, and may therefore facilitate use of the systems and methods described herein where a plurality of sensors are not already installed in an operating room or are not permanently installed in an operating room.

Figure 3:
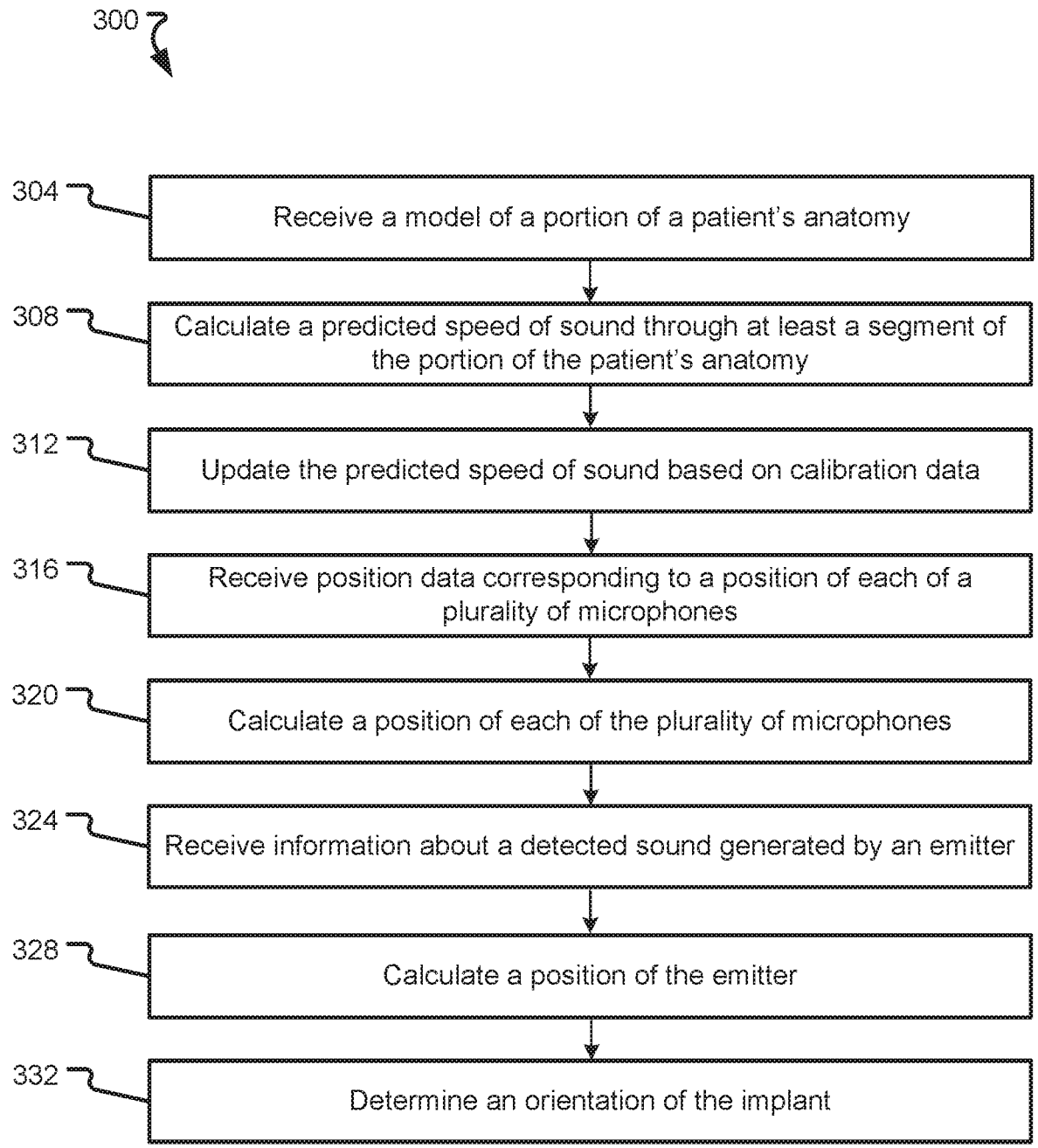
FIG. 3 is a flowchart of a method according to at least one embodiment of the present disclosure.

Turning now to FIG. 3, a method 300 for utilizing a robotic reference frame for navigation may be performed, for example, by at least one processor. The at least one processor may be the same as or similar to the processor(s) 104 of the computing device 102 described above. The at least one processor may be part of a robot (such as the robot 136) or part of a navigation system (such as the navigation system 160). A processor other than any processor described herein may also be used to execute the method 300. The at least one processor may perform the method 300 by executing instructions stored in a memory, such as the instructions 124 of the memory 116. The instructions may correspond to one or more steps of the method 300 described below. The instructions may cause the processor to execute one or more algorithms, such as the algorithms 128.

The method 300 comprises receiving a model of a portion of a patient's anatomy (step 304). The model may be a digital, 3D model of the portion of the patient's anatomy that is relevant to a planned surgical procedure. For example, if a surgical procedure is planned for a portion of a patient's spine, that the model may be a digital, 3D model of the patient's spine or a portion thereof, and may include details regarding anatomical features around the patient's spine. As another example, if the surgical procedure is planned for the patient's abdomen, then the model may be a digital, 3D model of the patient's abdomen, including the patient's organs located in the abdomen. The model may be generated based on one or more preoperative images, which may be, for example, CT scans, Mill images, X-ray images, or other images. The model may have been generated from a plurality of two-dimensional images. The model may be received from a database such as the database 164, via the cloud 168, or from another external source. The model may also be received from a memory such as the memory 116. The model may be received via a communication interface 108 and/or via a user interface 112. In some embodiments, the model may be received directly from an imaging device.

The method 300 also comprises calculating a predicted speed of sound through at least a segment of the portion of the patient's anatomy (step 308). Where sound will be used for triangulation purposes, a speed of sound through a segment of the patient's anatomy (e.g., a segment that extends from an emitter located somewhere within the portion of the patient's anatomy corresponding to the model received in the step 304, to an outer surface of the patient's anatomy) may be calculated. The calculating may comprise determining which materials lie along the segment (e.g., bony tissue, soft tissue, blood, stomach juices), measuring or otherwise determining a thickness of depth of each material along the segment, looking up (e.g., in a look-up table or other database) a speed of sound through each material, and then calculating a speed of sound along the entire segment based on the foregoing information. Thus, as a simple example, if the segment in question is determined to extend through two inches of bony tissue, one half inch of fatty tissue, and one sixteenth of an inch of skin tissue, then the calculating may comprise determining a speed of sound through each of bony tissue, fatty tissue, and skin tissue, and then based on the amount of each tissue through which a sound wave must pass and the determined speed of sound through each type of tissue, calculating how long it would take a sound wave to travel through the two inches of bony tissue at the speed of sound through bony tissue, one half inch of fatty tissue at the speed of sound through fatty tissue, and one sixteenth inch of skin tissue at the speed of sound through skin tissue. In some embodiments, an average speed of sound through anatomical tissue may be calculated, and a distance through which a sound wave must travel from an emitter located within the patient's anatomy to a surface of the patient's body may be divided by the average speed of sound through anatomical tissue to determine an amount of time that a sound wave will take to reach the surface of the patient's body.

In some embodiments, the predicted speed of sound may be calculated through a plurality of segments of the patient's anatomy. Also in some embodiments, the calculations may be based on a general or precise location of one or more of a plurality of sensors positioned to detect or receive the sound wave. Thus, for example, if one microphone is positioned directly above an operating table, and another is positioned directly to the side of an operating table, then a first predicted speed of sound may be calculated for a segment of the patient's anatomy that extends from a planned position of an emitter within the patient's anatomy to a surface of the patient's anatomy located above the planned position (e.g., in the direction of the microphone positioned directly above the operating table), and a second predicted speed of sound may be calculated for a segment of the patient's anatomy that extends from the planned position of the emitter to a surface of the patient's anatomy located to the side of the emitter (e.g., in the direction of the microphone positioned directly to the side of the operating table). In other embodiments, an average speed of sound may be utilized for the calculations of the step 308, and the model may be used to determine either a precise or an approximate distance through which a sound wave must travel through the patient's anatomical tissue before reaching a surface thereof and traveling through the air in the operating room.

The method 300 also comprises updating the predicted speed of sound based on calibration data (step 312). For example, an emitter such as the emitter 156 may be placed on one side of a patient's body, and a sensor such as the sensor 212 may be placed on an opposite side of the patient's body, with a known positional relationship between the emitter and the sensor. The emitter may generate a sound at a first known time, which may be detected by the sensor at a second known time. Based on the first known time, the second known time, and a known distance between the emitter and the sensor, a speed of sound through the patient's body may be calculated, and this calculated speed of sound may be utilized as calibration data for updating the predicted speed of sound calculated in the step 308.

The method 300 also comprises receiving position data corresponding to a position of each of a plurality of microphones (step 316). The position data may be relative to a single coordinate system, and may comprise information about a location of each of the plurality of microphones within the single coordinate system. In other embodiments, the position data may be relative to one or more of the other microphones in the plurality of microphones, such that a position of each microphone is known relative to a position of the others of the plurality of microphones, even if a position of the microphones relative to the operating room or to a more global coordinate system is not known. The position data may be comprise information about the actual position of each of the plurality of microphones, or information from which the actual position of each of the plurality of microphones may be calculated. The position data may in some embodiments comprise information about a pose of robotic or other articulated arm to which one or more of the plurality of microphones are attached.

The method 300 also comprising calculating a position of each of the plurality of microphones (step 320). Where the position data received in the step 316 comprises information from which the actual position of each of the plurality of microphones may be calculated (including, for example, information about a pose of a moveable arm from which a position of a microphone attached to the moveable arm may be calculated), then the step 320 of calculating a position of each of the plurality of microphones may be completed. The calculating may use one or more algorithms such as the algorithms 128 (which may be or comprise, for example, one or more algebraic, geometric, trigonometric, or other algorithms) to calculate a position of each of the plurality of microphones, whether relative to the others of the plurality of microphones or relative to a single common coordinate system (such as a predetermined coordinate system 120).

The method 300 also comprises receiving information about a detected signal generated by an emitter (step 324). Where, as here, the emitter is or comprises a speaker and the plurality of sensors being utilizes is a plurality of microphones, the detected signal is a sound signal. The detected signal may have a frequency that corresponds to a frequency to which the plurality of microphones are tuned or otherwise configured to detect. The detected signal may have a frequency that corresponds to a sole frequency at which the emitter is configured to generate sound waves, or a frequency selected from among a limited set of frequencies at which the emitter is configured to selectively generate sound waves. The detected signal may have one or more characteristics intended to distinguish the detected signal from one or more other sounds in an operating room environment. In some embodiments, for example, the detected signal may comprise a single pulse, while in other embodiments, the detected signal may comprise a series of pulses, which may or may not be equal in length and in time-spacing from a previous and/or subsequent pulse. The detected signal may, for example, have a frequency in the infrasound range or the ultrasound range, so as not to be heard by operating room staff. The detected signal may have a frequency in the acoustic range (between the infrasound and ultrasound ranges), but proximate a boundary of that range so as to reduce a likelihood that the signal will be heard by persons in the operating room. The detected signal may have a frequency selected to avoid interference with one or more instruments, tools, or other devices or systems in the operating room environment.

The information about the detected signal may be received all at once (e.g., as a collection of data generated by each of the plurality of microphones), or the information about the detected signal may be received over time (e.g., data generated by each of the plurality of microphones may be received based on when each of the plurality of microphones detects the signal). In the former instance, the information may comprise data corresponding to a time at which each of the plurality of microphones detected the signal. In the latter instance, the information may not comprise data corresponding to a time at which each of the plurality of microphones detected the signal.

Where the plurality of microphones are directional microphones (e.g., microphones configured to determine a direction from which a signal is received), the information about the detected signal may comprise information about the direction from which the signal was received from each of the plurality of microphones.

The emitter may be the same as or substantially similar to, for example, the emitter 156. The information about the detected signal may be received from the plurality of microphones, whether directly or via one or more communication interfaces, such as the communication interfaces 108. The information may be raw data corresponding to a detected signal generated by the emitter, or the information may be processed data corresponding to a detected signal generated by an emitter. For example, the information may simply be an electrical signal generated by each of the plurality of microphones upon the detected signal reaching each of the plurality of microphones. Alternatively, the information may be or comprise the result of amplifying, filtering, conditioning, and/or otherwise processing one or more such electrical signals.

The method 300 also comprises calculating a position of the emitter (step 328). The calculating may be based on the information received in the step 324. Where the information does not comprise data corresponding to a time at which each of the plurality of microphones detected the signal, the calculating may also be based on a time at which data from each of the plurality of microphones was received. The calculating may also be based on a predicted speed of sound calculated in the step 308, the updated predicted speed of sound from the step 312, and/or the model received in the step 304. The calculating may further be based on the position of each of the plurality of microphones, as received in the step 316 or as calculated in the step 320. The calculating may utilize one or more algorithms 128, including, for example, one or more trigonometric, geometric, or other mathematical equations or functions. The calculating comprises using triangulation methods based on known distances between or among the microphones as well as information about the speed of sound through one or more media to determine a position of the emitter (and thus of the implant, tool, anatomical feature, or other object to which the emitter is attached or otherwise secured).

The method 300 also comprises determining an orientation of the implant (step 332). Where the emitter comprises a plurality of speakers, each speaker may generate a signal (e.g., a sound wave), and each signal may be detected by the plurality of microphones. The signals may differ from each other in at least one characteristic, such that each signal can be distinguished from the other signals. A position of each speaker may then be calculated according to the step 328, and the calculated speaker positions may be used—together with information about, for example, a position of each speaker within or on the emitter—to determine an orientation of the emitter. Where the relative positioning of the emitter and the object to which the emitter is attached or otherwise secured is known (here, an implant), the orientation of the object may thus also be determined. In other words, the determining may be based on information about a plurality of detected signals, information about a position of each speaker within the emitter, and/or information about a relative position of the emitter and the object to which the emitter is attached or otherwise secured.

The present disclosure encompasses a number of variations on the method 300. For example, one or more of the steps of the method 300 may be omitted in embodiments of the present disclosure. More specifically, a method according to embodiments of the present disclosure may omit one or more of the steps 304, 308, 312, 316, 320, 324, and/or 332 while including the remaining steps of the method 300. The present disclosure also encompasses methods that additional steps beyond those described herein with respect to the method 300. In other words, the present disclosure encompasses methods that include more or fewer steps (including steps that are unique from those described herein) than the method 300. Additionally, although the method 300 is described in connection with an emitter comprising a speaker and a plurality of microphones configured to detected a sound emitted by the speaker, other embodiments of the present disclosure may utilize non-sound signals for triangulation to determine a position of the emitter (or of one or more speakers of the emitter, or of an object to which the emitter is attached). For example, embodiments of the present disclosure may utilize RF or other electromagnetic signals instead of sound signals, with a corresponding emitter and plurality of sensors. Additionally, while the method 300 is described based on the use of an active emitter and a plurality of sensors configured only to receive signals generated by a separate emitter, other embodiments of the present disclosure utilize a plurality of sensors that includes at least one transceiver capable of generating a signal, and either a passive emitter configured to reflect a signal so generated, or an active emitter configured to receive and respond to the signal. Thus, embodiments of the present disclosure may utilize RADAR, SONAR, ultrasound, or other technologies that utilize signal reflection or bounce-back to determine distance or other information from which a position of an object may be calculated or otherwise determined.

Additionally, although various steps of the method 300 are described in connection with information about a single detected sound, in embodiments of the present disclosure, a plurality of sounds may be detected, whether all from the same speaker, or from a plurality of speakers (each of which may generate one or more of the detected sounds). For example, where the emitter comprises three speakers, each speaker may detect a sound, and information about each of the detected sounds may be used for any purpose described herein (e.g., to determine position, orientation, movement, relative position, or otherwise). Each detected sound may be the same or different (e.g., different frequency, different amplitude, different pattern of pulses). As another example, each of a plurality of objects within the patient's body may have an emitter attached thereto, and one or more sounds may be generated by one or more speakers corresponding to each emitter. Again, information about these detected sounds may be used for any purpose described herein, and each detected sound may be the same or different.

The method 300 beneficially enables determination of a position and even an orientation of an emitter, as well as an object to which the emitter is attached or otherwise secured. The object may be a medical device, tool, or implant, or other foreign object (relative to the patient), or the object may be an anatomical feature of the patient. Moreover, the method 300 beneficially does not require the use of harmful radiation, nor does the method 300 require a line of sight between each of the plurality of sensors and the emitter. The method 300 may be accomplished automatically during a surgery, without manual intervention and without consuming valuable time of the operating room staff. The method 300 beneficially enables operating room staff to determine and/or track a position, orientation, and/or movement of one or more objects within a patient's body, thus enabling improved accuracy and safety during a surgical procedure.

Figure 4:
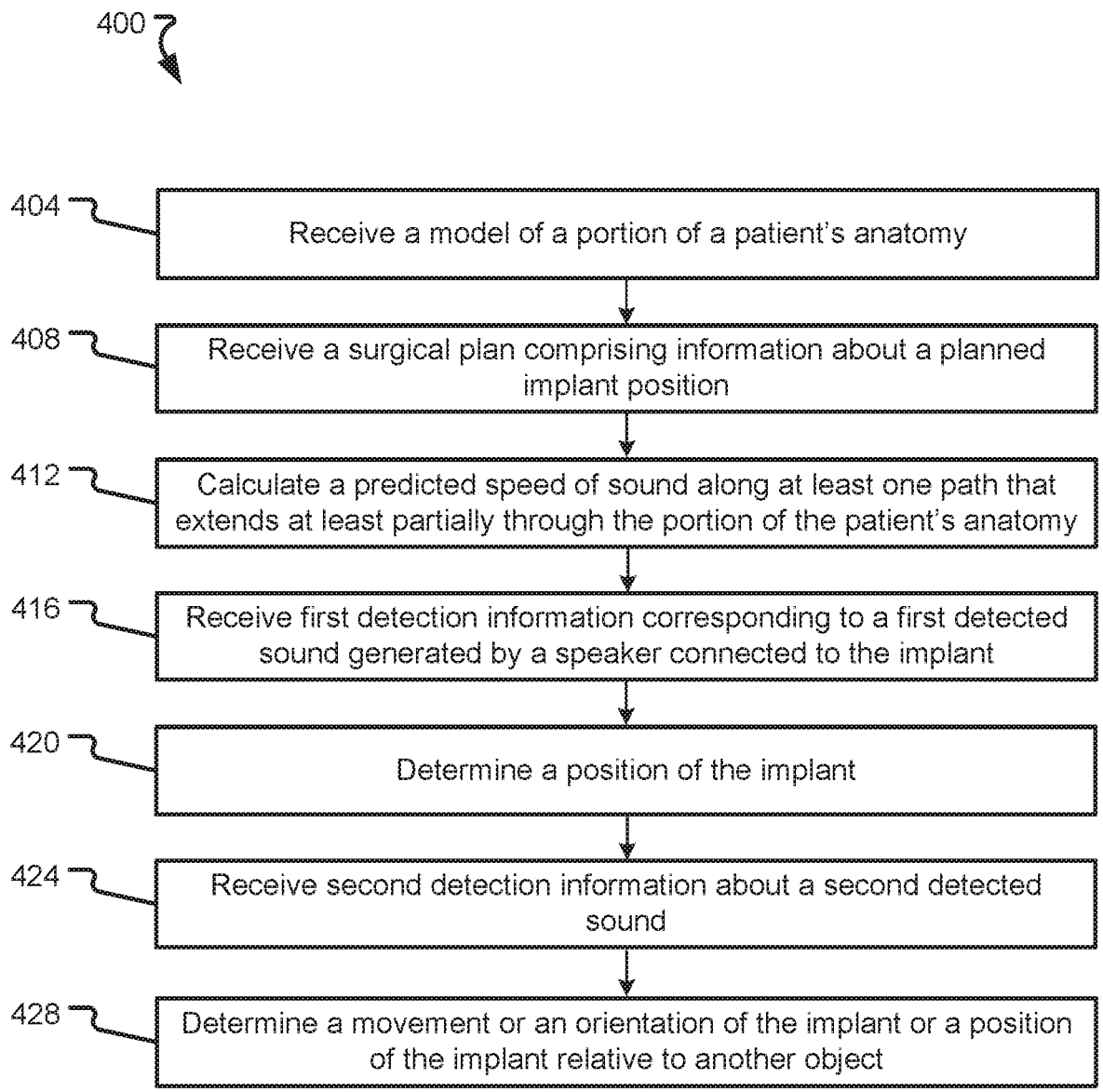
FIG. 4 is another flowchart of a method according to at least one embodiment of the present disclosure.

With reference now to FIG. 4, a method 400 of using triangulation to determine a position, movement, and/or orientation of an object comprises receiving a model of a portion of a patient's anatomy (step 404). The step 404 may be the same as or substantially similar to the step 304 described above.

The method 400 also comprises receiving a surgical plan comprising information about a planned implant position (step 408). The surgical plan may be received via a communication interface such as the communication interface 108, and may be received from or via a memory such as the memory 116, a database such as the database 164, and/or a cloud such as the cloud 168. The surgical plan may comprise information about one or more steps of a surgical procedure, including one or more planned positions of an implant during the surgical procedure. The one or more planned positions may correspond to planned positions of the implant relative to one or more anatomical features in the model of the portion of the patient's anatomy, or relative to a coordinate system such as a predetermined coordinate system 120. The surgical plan may be combined with or separate from the model of the patient's anatomy received in the step 404.

The method 400 also comprises calculating a predicted speed of sound along at least one path that extends at least partially through the portion of the patient's anatomy (step 412). The calculating the predicted speed of sound may be the same as or substantially similar to the step 308 described above in connection with the method 300. The calculating may be based at least in part on the information about the planned implant position, and may comprise calculating a predicted speed of sound along one or more paths extending from or proximate the planned implant position to a surface of the patient's body. The calculated predicted speed of sound may be updated based on calibration data, which may be generated and/or received before or during a surgical procedure corresponding to the surgical plan received in the step 408.

The method 400 also comprises receiving first detection information corresponding to a first detected sound generated by a speaker connected to the implant (step 416). The first detection information may be the same as or substantially similar to the information about the detected sound described above in connection with the step 324. The first detection information may comprise data received directly or indirectly from a plurality of sensors such as the plurality of sensors 132, which in this embodiment are a plurality of microphones.

The method 400 also comprises determining a position of the implant (step 420). The determining a position of the implant may be based on a calculated or otherwise determined position of the speaker (which may be calculated or otherwise determined in the same manner or in a substantially similar manner as the calculating a position of the emitter as described above in connection with the step 328), as well as based on information about a position of the speaker relative to a position of the implant (which information may be stored, for example, in a memory such as the memory 116, or received via a communication interface such as the communication interface 108, whether from or via a database such as the database 164, a cloud such as the cloud 168, or elsewhere). Calculating or otherwise determining a position of the speaker may be accomplished utilizing triangulation as well as the first detection information, the predicted speed of sound, information about a position of or distance between each of a plurality of microphones configured to detect sound generated by the speaker, and/or any other useful information.

The method 400 also comprises receiving second detection information about a second detected sound (step 424). Receiving the second detection information about a second detected sound may be the same as or similar to receiving the first detection information about the first detected sound, as described above in connection with the step 416. In the step 424, however, the second detected sound may be generated by the same speaker that generated the first detected sound; by a different speaker of the same emitter that comprised the speaker that generated the first sound; by a different speaker attached to the same implant (and not comprising part of the same emitter as the speaker that generated the first sound); or by a different speaker attached to a different object (e.g., medical device, tool, implant, or other foreign implant, or anatomical feature of the patient) than the speaker that generated the first sound.

The method 400 also comprises determining a movement or an orientation of the implant, or a position of the implant relative to another object (step 428). The determining may comprise first determining a position of the speaker that generated the second detected sound. The position of the speaker that generated the second detected sound may be determined in the same manner or in a substantially similar manner as described above in connection with the step 328. The determining (of the step 428) may also comprise determining a position of an object to which the speaker that generated the second detected sound is attached, which may be accomplished based on a determined position of the speaker that generated the second detected sound as well as based on information about a relative position of that speaker and the object to which that speaker is attached.

Where the second detected sound was generated by the same speaker as the first detected sound, the step 428 may comprise determining a movement of the implant. If the determined position from the step 420 differs from the determined position in the step 428, then the difference in determined positions corresponds to a movement of the speaker (and thus, of the implant to which the speaker is attached).

Where the second detected sound was generated by a different speaker of the same emitter that comprised the speaker that generated the first sound, the determined position from the step 420 together with the determined position of the step 428 may be used to determine an orientation of the emitter, from an orientation of the object to which the emitter is attached may also be determined (e.g., using information about a position of the emitter on the object to which the emitter is attached). Determining the orientation may be the same as or substantially similar to determining the orientation of an implant as described above in connection with the step 332.

Where the second detected sound was generated by a different speaker attached to the same implant (and not comprising part of the same emitter as the speaker that generated the first sound), an orientation of the implant may be determined directly, without first determining an orientation of the emitter. The orientation of the implant may be determined in the same manner or in a substantially similar manner as described above in connection with the step 332.

Where the second detected sound was generated by a different speaker attached to a different object (e.g., medical device, tool, implant, or other foreign implant, or anatomical feature of the patient) than the speaker that generated the first sound, then a position of the implant relative to a position of the object to which the different speaker is attached may be determined. Such information may be useful, for example, to determine a position of the implant relative to a position of an anatomical feature of the patient (e.g., where the implant needs to be positioned adjacent to or otherwise in relation to an anatomical feature of the patient), or to determine a position of a tool relative to a position of the implant (e.g., where a tool needs to be connected to the implant, or where a tool needs to avoid contacting the implant).

Each detected sound of the method 400 may have a unique frequency. In some embodiments, such as embodiments in which a single speaker generates more than one detected sound, each speaker may be configured to generate sound at a frequency that is unique from the frequency at which every other speaker is configured to generate sound.

The present disclosure encompasses a number of variations on the method 400. For example, although the method 400 is described above with respect to the use of speakers and a plurality of microphones configured to detect one or more sounds generated by the speakers, in other embodiments the method 400 may utilize, for example, RF or other electromagnetic waves rather than sound waves, with corresponding signal generators (instead of speakers) and sensors (instead of microphones). The method 400 may also be implemented with a passive emitter rather than a speaker, which passive emitter may be configured simply to reflect a signal generated outside of the patient's body (whether by one or more of the plurality of sensors or by a separate emitter, the position of which is known). Such embodiments may utilize ultrasound, RADAR, SONAR, or other technologies for determining a position and/or orientation of the emitter.

Additionally, although the method 400 only explicitly describes the use of information about a first detected sound and information about a second detected sound, in embodiments of the present disclosure, a plurality of sounds may be detected, whether all from the same speaker, or from a plurality of speakers (each of which may generate one or more of the detected sounds). For example, where an emitter attached to the implant comprises three speakers, and additional emitters comprising three speakers each are attached to a plurality of anatomical features in the area where the implant is to be inserted as well as to one or more tools that will be used during a surgical procedure involving the implant (or involving a portion of the patient's anatomy in which the implant is positioned), then a position and/or orientation of each of the emitters (and thus of each of the objects to which the emitters are attached) may be determined, as well as any movement of such emitters (and thus of the objects to which the emitters are attached), and a position of one emitter relative to any other emitter (and thus of one object to which an emitter is attached relative to any other object to which another emitter is attached).

Like the method 300, the method 400 beneficially enables determination of a position and even an orientation of an emitter, as well as an object to which the emitter is attached or otherwise secured. The method 400 also enables detection of movement of an emitter (as well as an object to which the emitter is attached) and of a position of one emitter relative to a position of another emitter (as well as objects to which the emitters are attached). Moreover, the method 400 beneficially does not require the use of harmful radiation, nor does the method 400 require a line of sight between each of the plurality of sensors and the emitter. The method 400 may be accomplished automatically during a surgery, without manual intervention and without consuming valuable time of the operating room staff. The method 400 beneficially enables operating room staff to determine and/or track a position, orientation, and/or movement of one or more objects within a patient's body, thus enabling improved accuracy and safety during a surgical procedure.

Any signal generator described herein (such as the signal generator 176) may be used in place of any speaker described herein, and any sensor described herein (such as the sensor 212) may be used in place of any microphone described herein, provided that the sensor is configured to receive or detect signals generated by the signal generator, and the signal generator is configured to generate signals detectable and receivable by the sensor.

Although both of the methods 300 and 400 are described as comprising the step of receiving a model of a portion of a patient's anatomy, and also as comprising the step of calculating a predicted speed of sound through at least a segment of the portion of the patient's anatomy (method 300) or along at least one path that extends at least partially through the portion of the patient's anatomy (method 400), embodiments of the present disclosure do not require either or both of these limitations. For example, when a surgical procedure is an open procedure (rather than, for example, a minimally invasive procedure), a line of sight may exist between the emitter (whether a speaker or otherwise) and the sensors (whether microphones or otherwise), such that the signal generated by the emitter need not travel through the patient's anatomy to reach the sensor, and no adjustment need be made for the speed of the signal based on interference from the patient's anatomy. Also, although the methods 300 and 400 are described as including steps regarding calculating a predicted speed of sound to address interference from the patient's anatomy, embodiments that use other types of signals may comprise corresponding steps regarding calculating a predicted speed at which a signal of the type in question will travel through the patient's anatomy.

As may be appreciated based on the foregoing disclosure, the present disclosure encompasses methods with fewer than all of the steps identified in FIGS. 3 and 4 (and the corresponding description of the methods 300 and 400), as well as methods that include additional steps beyond those identified in FIGS. 3 and 4 (and the corresponding description of the methods 300 and 400). The present disclosure also encompasses methods that combine one or more steps of the method 300 with one or more steps of the method 400 or vice versa.

Embodiments of the present disclosure may also be used to located items not positioned within a patient's body. For example, an emitter could be attached to each of one or more robots, instruments, tools, imaging devices, and/or other systems or devices within an operating room, and the systems and methods described herein may be used to track a location or position of each such object during a surgical procedure. In such embodiments, the tracked location or position may be used to ensure that no unwanted objects are placed in or left behind in a patient's body; to enable a robot operating autonomously or semi-autonomously to avoid a collision with another tracked object; to facilitate proper positioning of a robot, an imaging device, a medical instrument or tool, or any other object relative to another object; or for any other useful purpose. Where an emitter is placed on one or more anatomical features of a patient, embodiments of the present disclosure may be used for segmental tracking.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A surgical positioning system, comprising:
   an emitter secured to a medical implant, comprising:
      a speaker; and
      a power source;
   at least three microphones;
   at least one processor; and
   a memory storing instructions for execution by the processor that, when executed, cause the processor to:
      receive, from each of the at least three microphones, information about a detected sound;
      receive a model of a portion of a patient's anatomy, the model being generated from one or more preoperative images that include the portion of the patient's anatomy;
      calculate, based on the model, a predicted speed of sound through at least a segment of the portion of the patient's anatomy by:
         determining, using the model, which materials lie along the segment;
         measuring, within the model, a thickness of each material that lies along the segment;
         determining a speed of sound through each material that lies along the segment; and
         calculating the predicted speed of sound based on the thickness of each material and the speed of sound of each material that lies along the segment; and
      calculate, based on position information corresponding to each of the at least three microphones, the predicted speed of sound, and the received information, a position of the implant.

2. The surgical positioning system of claim 1, wherein the memory stores additional instructions for execution by the at least one processor that, when executed, further cause the at least one processor to:
   determine the speed of sound through each material that lies along the segment by retrieving the speed of sound of each material from a database.

3. The surgical positioning system of claim 1, wherein the memory stores additional instructions for execution by the at least one processor that, when executed, further cause the at least one processor to:
   update the predicted speed of sound based on calibration data corresponding to a calibration sound generated by the emitter and detected by each of the at least three microphones.

4. The surgical positioning system of claim 3, wherein the calculating the position of the implant is further based on the updated predicted speed of sound.

5. The surgical positioning system of claim 2, wherein each of the at least three microphones is mounted in a fixed position relative to any others of the at least three microphones.

6. The surgical positioning system of claim 1, wherein the detected sound has a frequency less than 20 kHz.

7. The surgical positioning system of claim 1, wherein the detected sound has a frequency less than 20 Hz.

8. The surgical positioning system of claim 1, wherein at least one of the at least three microphones is mounted to a movable arm, and the memory stores additional instructions for execution by the at least one processor that, when executed, further cause the at least one processor to:
   receive arm position data corresponding to a position of the movable arm; and
   calculate, based at least in part on the arm position data, a location of each of the at least three microphones.

9. The surgical positioning system of claim 1, wherein the position information for each of the at least three microphones comprises data about a position of each of the at least three microphones relative to the others of the at least three microphones, and the calculated emitter position is relative to the positions of the at least three microphones.

10. The surgical positioning system of claim 1, wherein the position information for each of the at least three microphones is relative to a common coordinate system.

11. The surgical positioning system of claim 1, wherein the emitter comprises a plurality of speakers, each speaker is configured to emit sound at a different frequency than the other speakers in the plurality of speakers, the received information comprises information about a detected sound generated by each of the plurality of speakers, respectively, and the memory stores additional instructions for execution by the at least one processor that, when executed, further cause the at least one processor to:
   determine an orientation of the implant based at least in part on the received information.

12. A method of locating an object during a surgery, comprising:
   receiving a model of a portion of a patient's anatomy;
   receiving a surgical plan comprising information about a planned position of an implant within the portion of the patient's anatomy;
   calculating, based on the planned position of the implant and the model, a predicted speed of sound along at least one path that extends at least partially through the portion of the patient's anatomy, the predicted speed of sound being calculated by:

determining, using the model, which materials lie along the at least one path;

measuring, within the model, a thickness of each material that lies along the at least one path;

determining a speed of sound through each material that lies along the at least one path; and calculating the predicted speed of sound based on the thickness of each material and the speed of sound of each material that lies along the at least one path;

receiving, from at least three microphones, detection information about a detected sound generated by a speaker secured to the implant; and determining, based on the predicted speed of sound and the detection information, a position of the implant.

13. The method of claim 12, wherein the detection information comprises first detection information about a first detected sound generated by the speaker at a first time, the method further comprising:

receiving, from the at least three microphones, second detection information about a second detected sound generated by the speaker, the second detected sound generated at a second time after the first time; and determining, based on first detection information and the second detection information, a movement of the implant.

14. The method of claim 12, wherein the detection information corresponds to detected sounds generated by a plurality of speakers secured to the implant, the method further comprising:

determining, based on the predicted speed of sound and the detection information, an orientation of the implant.

15. The method of claim 14, wherein each of the detected sounds has a unique frequency relative to any others of the detected sounds.

16. The method of claim 12, wherein the determining is further based on location information corresponding to a location of each of the at least three microphones.

17. The method of claim 12, wherein the detection information comprises first detection information about a first detected sound generated by the speaker at a first time, the method further comprising:

receiving, from the at least three microphones, second detection information about a second detected sound generated by a second speaker affixed to an anatomical element of the patient; and determining, based on first detection information and the second detection information, a position of the implant relative to the anatomical element.

18. A surgical triangulation system comprising:

a plurality of microphones configured to be installed in fixed locations about an operating room;

an emitter configured to be secured to an internal anatomical feature of a patient or an implant, the emitter comprising:

a speaker; and a power source;

at least one processor; and a memory storing instructions for execution by the at least one processor that, when executed, cause the at least one processor to:

receive a surgical plan comprising information about a portion of the patient's anatomy;

receive a model of the portion of the patient's anatomy, the model being generated from one or more preoperative images that include the portion of the patient's anatomy;

calculate, based on the model, a predicted speed of sound through at least a segment of the portion of the patient's anatomy by:

determining, using the model, which materials lie along the segment;

measuring, within the model, a thickness of each material that lies along the segment;

determining a speed of sound through each material that lies along the segment; and calculating the predicted speed of sound based on the thickness of each material and the speed of sound of each material that lies along the segment;

receive, from the plurality of microphones, sound information about a sound detected by the plurality of microphones and generated by the speaker; and calculate, based on the surgical plan, the predicted speed of sound, the sound information, and information about the fixed locations of the plurality of microphones, a position of the emitter.

19. The surgical triangulation system of claim 18, wherein the emitter is biocompatible.

20. The surgical triangulation system of claim 18, wherein emitter comprises a second speaker, and the memory stores additional instructions for execution by the at least one processor that, when executed, further cause the at least one processor to:

receive, from the plurality of microphones, second sound information about a second sound detected by the plurality of microphones and generated by the second speaker; and calculate, based on the surgical plan, the second sound information, and the information about the fixed locations of the plurality of microphones, an orientation of the emitter.

* * * * *